United States Patent [19]

Blank

[11] Patent Number: 5,232,703
[45] Date of Patent: Aug. 3, 1993

[54] ESTRADIOL COMPOSITIONS AND METHODS FOR TOPICAL APPLICATION

[76] Inventor: Izhak Blank, 4 Simtat Arnon, Kiriat Ono, Israel

[21] Appl. No.: 868,981

[22] Filed: Apr. 14, 1992

Related U.S. Application Data

[60] Division of Ser. No. 732,348, Jul. 17, 1991, Pat. No. 5,128,138, which is a continuation of Ser. No. 461,676, Jan. 8, 1990, abandoned.

[30] Foreign Application Priority Data

Jul. 21, 1989 [IL] Israel ............................ 91067

[51] Int. Cl.$^5$ .............................................. A61F 13/00
[52] U.S. Cl. ............................ 424/449; 424/45; 424/447; 424/448; 514/944; 514/946; 514/947; 239/338
[58] Field of Search ............ 424/447, 448, 449, 45; 514/946, 947, 944

[56] References Cited

U.S. PATENT DOCUMENTS

| | | | |
|---|---|---|---|
| 2,776,924 | 1/1957 | Martin | 167/82 |
| 2,904,810 | 9/1959 | Dence | 401/213 |
| 3,214,338 | 10/1965 | Ehrlich | 167/63 |
| 3,287,222 | 11/1966 | Larde et al. | 167/84 |
| 3,608,070 | 9/1971 | Nouvel | 424/80 |
| 3,803,300 | 4/1974 | Pospischil | 424/28 |
| 3,948,262 | 4/1976 | Zaffaroni | 128/260 |
| 3,972,995 | 8/1976 | Tsuk et al. | 424/28 |
| 4,091,091 | 5/1978 | Terrill | 424/80 |
| 4,144,317 | 3/1979 | Higuchi et al. | 424/21 |
| 4,210,633 | 7/1989 | Takruri et al. | 424/80 |
| 4,379,454 | 4/1983 | Campbell et al. | 604/897 |
| 4,383,993 | 5/1983 | Hussain et al. | 424/239 |

(List continued on next page.)

FOREIGN PATENT DOCUMENTS

| | | |
|---|---|---|
| 0054279 | 6/1982 | European Pat. Off. |
| 0181970 | 5/1986 | European Pat. Off. |
| 0364211 | 4/1990 | European Pat. Off. |
| 0371496 | 6/1990 | European Pat. Off. |
| 1467792 | 2/1968 | Fed. Rep. of Germany |
| 2301664 | 8/1974 | Fed. Rep. of Germany |

(List continued on next page.)

OTHER PUBLICATIONS

W. R. Good et al., "A new Transdermal Delivery System for Estradiol", *Journal of Controlled Release*, 2, pp. 89–97 (1985).

R. H. Guy et al., "Transdermal Drug Delivery: A Perspective", *Journal of Controlled Release*, 4, pp. 237–251 (1987).

(List continued on next page.)

*Primary Examiner*—Thurman K. Page
*Assistant Examiner*—D. Gabrielle Phelan
*Attorney, Agent, or Firm*—Richard M. Barnes; John J. Cassingham

[57] ABSTRACT

A mixture of estradiol or other estrogen and an uncrosslinked, water-insoluble vinylpyrrolidone copolymer provides a matrix which gradually releases the medicament upon application to the skin of a patient in the form of an ointment, gel or film. The polymer provides for the slow and sustained release of the medicament upon topical application to the skin so that the concentration of drug in the blood plasma of the patient is maintained within the levels required for clinical efficacy.

20 Claims, No Drawings

U.S. PATENT DOCUMENTS

| | | | |
|---|---|---|---|
| 4,436,738 | 3/1984 | Bequette et al. | 424/238 |
| 4,482,534 | 11/1984 | Blank | 424/28 |
| 4,533,540 | 8/1985 | Blank | 424/28 |
| 4,687,481 | 8/1987 | Nuwayser | 604/897 |
| 4,788,062 | 11/1988 | Gale | 424/449 |
| 4,889,709 | 12/1989 | Mackles | 424/45 |
| 5,049,388 | 9/1991 | Knight | 424/450 |
| 5,130,137 | 7/1992 | Crowley, Jr. | 424/422 |

FOREIGN PATENT DOCUMENTS

| | | |
|---|---|---|
| 2634004 | 2/1978 | Fed. Rep. of Germany . |
| 8907951 | 9/1989 | PCT Int'l Appl. . |
| 1380171 | 1/1975 | United Kingdom . |
| 1427881 | 3/1976 | United Kingdom . |
| 2021610 | 12/1979 | United Kingdom . |

OTHER PUBLICATIONS

J. Holst et al., "A Comparison of Liver Protein Induction In Postmenopausal Women During Oral And Percutaneous Oestrogen Replacement Therapy", *Br. J. Obstet. Gynecol.*, 90, pp. 355–360 (1983).

R. E. Lacey et al., "Factors Affecting The Release of Steroids From Silicones" in Controlled Relese of Biologically Active Agents, Edited by A. C. Tanquary and R. E. Lacey, pp. 117–144 (Plenum Press 1974).

L. R. Laufer et al., "Estrogen Replacement Therapy By Transdermal Estradiol Administration", *Amer. J. Obstet. Gynecol.*, 146, pp. 533–540 (1983).

M. L. Padwick et al., "Efficacy, Acceptability, And Metabolic Effects Of Transdermal Estradiol In The Management Of Postmenopausal Women", *Amer. J. Obstet. Gynecol.*, 152, pp. 1085–1091 (1985).

V. A. Place et al., "A Double-Blind Comparative Study of Estraderm and Premarin in the Amelioration of Postmenopausal Symptoms", *Amer. J. Obstet. Gynecol.*, 152, pp. 1092–1099 (1985).

M. S. Powers et al., "Pharmacokinetics and pharmacodynamics of Transdermal Dosage Forms of 17 Beta-Estradiol: Comparison with Conventional Oral Estrogens used for Hormone Replacement", *Amer. J. Obstet. Gynecol.*, 152, pp. 1099–1106 (1985).

D. E. Resetarits et al., "Dissolution Behavior of 17 Beta-Estradiol ($E_2$) From Providone Coprecipitates: Comparison with Microcrystalline and Macrocrystalline $E_2$", *Intl. J. Pharm.*, 2, pp. 113–123 (1979).

L. Schenkel et al., "Transdermal Absorption of Estradiol From Body Sites Is Comparable", *Journal of Controlled Release*, 4, pp. 195–201 (1986).

K. A. Steingold et al., "Treatment Of Hot Flashes With Transdermal Estradiol Administration", *J. Clin. Endocrin. Metab.*, 61, pp. 627–632 (1985).

ESTRADIOL COMPOSITIONS AND METHODS FOR TOPICAL APPLICATION

This is a division of application Ser. No. 732,348, filed Jul. 17, 1991, now U.S. Pat. No. 5,128,138 which is a continuation of U.S. application Ser. No. 461,676, filed Jan. 8, 1990, now abandoned.

BACKGROUND OF THE INVENTION

1. Field of Invention

This invention relates to novel compositions of matter for topical application to humans and methods for providing therefrom a controlled dosage of 17-$\beta$-estradiol. The novel compositions comprise estradiol and a polymer in a form adapted for the slow and gradual release of the medicament so that the concentration of drug in the blood plasma of the patient is maintained within levels desirable for optimum clinical efficacy.

2. Description of the Prior Art

Knowledge of the endocrinological role of estradiol dates from the early part of this century. Its relation to the menstrual cycle was established in the 1920s and its chemical structure was elucidated in the 1930s.

When the ovaries do not function properly due to age, i.e. menopause, or disease, or have been removed, the consequent lack of endogenous estradiol may produce a number of symptoms, such as hot flashes, pain and increased hypocalcemia, eventually leading to osteoporosis.

One way of avoiding or alleviating these symptoms is by estrogen replacement therapy, i.e. by giving a compensatory dose of estrogen to the patient. This treatment is not without danger, since it has been established by various researchers that in women taking exogenous estrogens, there is an increased risk of endometrial cancer, estimated to be between 4.5 to 13.9 times greater than in women not taking exogenous estrogen. The risk is related to dosage and duration of use. Other side effects due to the intake of estradiol may be cholelithiasis (gall bladder disease) and thromboembolic disease due to increase in lipoproteins and triglycerides in the blood.

As a result of the increase in the average age of the human population during the last few decades, there are more female patients suffering from post-menopausal symptoms and osteoporosis and, therefore, there is a growing need for this form of therapy. However, due to the sometimes dangerous side effects mentioned hereinbefore, treatment requires a very fine tuning of the dosage, i.e. the blood levels of the drug are kept at the minimum required for clinical efficacy.

The concentration of estradiol required for clinical effectiveness has been shown to be between 50 and 120 picograms per milliliter (pg/l) of plasma. At 60 pg/l a reduction of about 50% of the hot flashes was observed and at about 120 pg/ml they totally disappeared.

Various methods are in use or have been proposed for the estradiol replacement therapy, e.g. tablets, aqueous suspensions for injection, implants and patches for transdermal application.

Oral therapy, using tablets, is most convenient for the patient but the effect is rather short since the half-life of estradiol in the plasma is only one hour and up to three doses per day may be required to maintain therapeutically effective levels. The first pass inactivation of estradiol is very high, its oral availability being only about 30%. This leads to accumulation in the body of large quantities of estrone and other estrogens.

Resetarits et al (International Journal of Pharmaceutics, 2, 113–123 (1979)) reported that the dissolution rate of estradiolpolyvinylpyrrolidone "coprecipitates", prepared by dissolving both components in ethanol and subsequently removing the solvent in vacuo, was appreciably higher than that of microcrystalline estradiol. There was no evidence that estradiol and polyvinylpyrrolidone formed complexes in the solid state and it was concluded that in the "coprecipitate" the estradiol exists in a more water-soluble, high energy form of the drug. It was suggested that this may increase the systemic availability of the estradiol and reduce the extensive pre-systemic metabolism after oral administration.

The use of parenteral injections and implants or pellets, while avoiding the first pass loss, is much less convenient for the patient and, therefore, the use of these forms of therapy is not popular.

The administration of estradiol from a dosage form adapted for nasal delivery, e.g. solutions, suspensions, gels and ointments, is disclosed in U.S. Pat. No. 4,383,993. The dosage form consists of estradiol and a pharmaceutically acceptable nasal carrier, e.g. a mixture of water, an emulsifier and, if desired, a gelling agent.

Estradiol, like other estrogens, is readily absorbed through the skin and since, as indicated hereinbefore, very low concentrations (around 100 pg/ml) are required for clinical efficacy, this renders it an excellent candidate for transdermal application. Schenkel, Barlier, Riera and Barner (Journal of Controlled Release, 4, 195–201 (1986)) have shown that transdermal application of estradiol to different body sites results in comparable absorption.

Patches for transdermal application generally involve membrane-control of the delivery of the drug. U.S. Pat. No. 4,379,454 discloses an adhesive patch in which estradiol and ethanol simultaneously permeate through an ethylene-vinyl acetate copolymer membrane from a gelled estradiol-ethanol mixture which is in contact with the membrane. The ethanol enhances the rate of percutaneous absorption of the estradiol.

Transdermal delivery systems for estradiol have been reviewed by Good, Powers, Campbell and Schenkel (Journal of Controlled Release, 2, 89–97 (1985)) and Guy and Hadgraft (Journal of Controlled Release, 4, 237–251 (1987)).

The factors affecting the diffusion of steriods, including estradiol, through crosslinked polydimethylsiloxane membranes have been reported by Lacey and Cowsar in "Controlled Release of Biologically Active Agents", Tanquary and Lacey, eds, Plenum Press, New York, pp. 117–144 (1974).

The present invention is directed towards improvements in the transdermal delivery of estradiol wherein compositions containing the steroid, upon topical application, will provide a slow and sustained release of the estradiol so as to maintain the desired level of the drug in the blood of the patient. This is accomplished by the incorporation of uncrosslinked, water-insoluble vinylpyrrolidone copolymers in the compositions.

The use of water-soluble polyvinylpyrrolidone in conjunction with various medicaments has been disclosed in a number of patents. Thus, German DOS 2,301,664 and British Patent No. 1,427,881 disclose the prolongation of the storage stability of nitroglycerin by the addition of polyvinylpyrrolidone. U.S. Pat. No.

4,091,091 describes the stabilization of nitroglycerin against tablet-to-tablet migration by the incorporation of water-soluble polyvinylpyrrolidone in the mixture of a water-soluble excipient and nitroglycerin, while retaining the rapid solubility of the tablet in the mouth.

The release of nitroglycerin as a result of the water-solubility of vinylpyrrolidone homopolymer or copolymers has also been utilized in an antianginal film or plate. Thus, British Patent Application No. 2021610A discloses that a thin film containing nitroglycerin, a water-soluble homopolymer or copolymer of acrylamide and/or vinylpyrrolidone and, optionally a dispersed solid fat, is applied to a site in the mouth and releases the medicament at a rate which is dependent upon the rate of solution of the polymer.

The prior art teaches that water-soluble vinylpyrrolidone homopolymer complexes with nitroglycerin in a solid tablet or film and reduces the volatility and migration of the medicament without reducing the availability of the drug in an aqueous environment.

U.S. Pat. No. 4,482,534 discloses that the incorporation of water-insoluble vinylpyrrolidone homopolymer or copolymers in an ointment, gel or film containing nitroglycerin provides increased stability and reduced volatility of the nitroglycerin, while permitting slow release of the drug when applied topically to the skin.

The use of water-soluble polyvinylpyrrolidone in conjunction with medicaments other than nitroglycerin has been disclosed in a number of patents. Thus, U.S. Pat. No. 3,972,995 discloses a buccal dosage form in which the water-soluble homopolymer functions as a binder in an adhesive layer. U.S. Pat. No. 3,214,338 discloses a topical ointment in which the water-soluble homopolymer is added to an emulsifiable polyvinyl acetate powder. U.S. Pat. No. 3,803,300 discloses a film-forming ointment containing water-soluble vinylpyrrolidone homopolymer or copolymers. U.S. Pat. No. 3,287,222 discloses the use of the homopolymer as a water-soluble plasticizer in an impregnating solution for a synthetic fiber medical dressing. U.S. Pat. No. 4,210,633 discloses a water-soluble medicated film containing the water-soluble homopolymer. U.S. Pat. No. 3,608,070 discloses a surgical dressing which is an ointment containing a vinylpyrrolidone copolymer, a thixotropic agent, a water-soluble plasticizer and a solvent such as aqueous ethanol. The film formed on drying the ointment is readily soluble in water. U.S. Pat. No. 2,776,924 discloses the use of water-soluble polyvinylpyrrolidone to inhibit adverse reactions from therapeutic agents in topical application.

In these prior art disclosures with medicaments other than nitroglycerin, vinylpyrrolidone polymers are used because of their film-forming ability and/or water solubility. The rapid solubilization of the polymer results in rapid release of the medicament.

The prior art discloses that the use of water-insoluble, crosslinked polyvinylpyrrolidone also promotes the rapid release of medicament. Thus, British Patent No. 1,380,171 discloses the use of crosslinked, water-insoluble polyvinylpyrrolidone in medicinal tablets containing a drug, to promote rapid disintegration of the tablet in aqueous fluids and increase the availability of the drug. Examples are provided which illustrate that the presence of water-insoluble polyvinylpyrrolidone results in more rapid disintegration and release of the drug as compared with the water-soluble polymer. German Patent Application 2,634,004 discloses the use of crosslinked, insoluble polyvinylpyrrolidone as a carrier material for poorly soluble medicaments in order to accelerate the release thereof when administered orally. German Patent Application 1,467,792 discloses the use of crosslinked polyvinylpyrrolidone as a disintegration agent to increase the rate of disintegration of a tablet to promotes the extremely rapid release of the drug therein in the digestive tract.

SUMMARY OF THE INVENTION

The prior art teaches that water-soluble polyvinylpyrrolidone complexes with nitroglycerin in a solid tablet or film to reduce the volatility without reducing the availability of the drug, when the composition is placed in contact with water. The prior art also teaches that the presence of water-insoluble polyvinylpyrrolidone promotes even more rapid release of a medicament.

The prior art further teaches that estradiol, in contrast to nitroglycerin, does not complex with water-soluble polyvinylpyrrolidone in the solid state and is more water-soluble in the presence than in the absence of the polymer.

Surprisingly, it has now been discovered that the incorporation of an uncrosslinked, water-insoluble vinylpyrrolidone copolymer in an ointment, gel or film containing estradiol permits slow release of the drug when applied topically to the skin.

It has further been discovered that the delivery of estradiol from a composition which contains a water-insoluble vinylpyrrolidone copolymer and is applied directly to the skin without an intervening membrane, maintains blood levels of the drug at the concentration required for clinical efficacy.

It has further been discovered that ointments with sustained release characteristics can be prepared by the admixture of a dispersion or solution of a water-insoluble vinylpyrrolidone copolymer with an estradiol solution and a conventional hydrophobic base such as vasoline, lanolin and the like.

It has further been discovered that films with sustained release characteristics can be prepared from a solution containing a water-insoluble vinylpyrrolidone copolymer and estradiol, wherein the solution is applied per se or after thickening.

DETAILED DESCRIPTION OF THE INVENTION

According to the present invention, it has now been found that important advantages and improvements over prior art compositions containing 17$\beta$-estradiol and methods of topical application thereof can be obtained by admixture with an uncrosslinked, water-insoluble vinylpyrrolidone copolymer.

Water-insoluble copolymers of vinylpyrrolidone, which may be used in the practice of this invention, may be prepared by the copolymerization of vinylpyrrolidone with one or more appropriate comonomers in the proportions which yield water-insoluble, uncrosslinked copolymers. Suitable comonomers include acrylic esters, methacrylic esters, vinyl esters, crotonic esters, vinyl ethers, maleic half esters and diesters, vinylene carbonate, styrene, allyl esters, allyl ethers, etc. Other comonomers which are capable of copolymerizing with vinylpyrrolidone and are well known to those skilled in the art may also be used. Toxicological considerations restrict the choice of monomers to those which yield copolymers having a demonstrated lack of toxicological side-effects on topical application to the skin.

The acrylic, methacrylic, crotonic and maleic esters which may be used in the preparation of the water-insoluble vinylpyrrolidone copolymers which are effective in the practice of the present invention, include the esters of $C_1$–$C_{40}$ linear, branched or cyclic alkanols, aralkanols, phenols and substituted phenols. The copolymers of vinylpyrrolidone and the acrylic, methacrylic, crotonic and maleic esters may be made by copolymerization of vinylpyrrolidone with the appropriate ester or by esterification of copolymers of vinylpyrrolidone and acrylic, methacrylic, crotonic and maleic acid or anhydrides, with the appropriate hydroxy-containing compound. Unesterified carboxylic acid functionality may be retained in the copolymer.

The vinyl esters and allyl esters which may be used in the preparation of the water-insoluble vinylpyrrolidone copolymers which are useful in the practice of this invention, include the esters of $C_1$–$C_{40}$ linear, branched or cyclic aliphatic, araliphatic or aromatic carboxylic acids. The copolymers of vinylpyrrolidone and the vinyl esters may be prepared by copolymerization of vinylpyrrolidone with the appropriate vinyl ester or by transesterification of copolymers of vinylpyrrolidone and vinyl acetate or other vinyl esters or by esterification of hydrolyzed copolymers of vinylpyrrolidone and vinyl acetate or other vinyl esters. The copolymers of vinylpyrrolidone and allyl esters may also be prepared either by direct copolymerization or by transesterification or esterification, analogous to the preparation of vinyl ester copolymers with vinylpyrrolidone.

Graft copolymers made by grafting vinyl monomers onto polyvinylpyrrolidone may also be used, e.g. graft copolymers of polyvinylpyrrolidone with acrylic esters, methacrylic esters, styrene, vinyl acetate and the like.

The water-insoluble copolymers of vinylpyrrolidone which may be used in the practice of the present invention, may be prepared by any of the conventional methods known in the art, including bulk, solution, emulsion, suspension or dispersion polymerization, with appropriate free radical catalysts such as peroxygen compounds, azo compounds, redox systems, radiation and other catalytic techniques for initiating free radical polymerization. Since the method of polymerization is not an integral part of the practice of the present invention, any suitable method known to those skilled in the art may be used.

The amount of one or more comonomers in the water-insoluble vinylpyrrolidone copolymers which are useful in the practice of the present invention, may be varied from 0.1 to 90% by weight. The actual amount is determined by the nature of the comonomer and the concentration necessary to produce a water-insoluble copolymer.

The drug used in the practice of the present invention may be 17$\beta$-estradiol or its esters such as estradiol benzoate, cypionate, valerate or other derivatives such as ethinylestradiol. However, the preferred drug is 17$\beta$-estradiol.

The estradiol compositions which are useful in the practice of the present invention and provide sustained release of the medicament, may be prepared by dissolving or dispersing the water-insoluble vinylpyrrolidone copolymer in a solvent such as isopropanol, ethanol or an alcohol-water mixture, and admixing the polymer solution or dispersion with estradiol per se or as an estradiol solution in alcohol.

The solution of uncrosslinked, water-insoluble vinylpyrrolidone copolymer and estradiol, in the presence or absence of an excipient, may be cast on a suitable surface and the solvent evaporated under ambient pressure or in vacuo, at ambient or slightly elevated temperature. The resultant film on the substrate surface or after removal from the substrate, contains estradiol and may be cut into strips or tapes which can be affixed to the skin of a patient for sustained release of the medicament.

The solution of uncrosslinked, water-insoluble vinylpyrrolidone copolymer and estradiol may be applied directly to the skin of the patient and permitted to evaporate to form a film thereon, containing estradiol. The latter is slowly released from the film and absorbed into the skin of the patient.

The solution of vinylpyrrolidone copolymer and estradiol may be conveniently applied to the skin using an aerosol formulation containing one or more low boiling propellants. Although fluorocarbon propellants such as trichloromonofluoromethane, dichlorodifluoromethane and dichlorotetrafluoroethane are particularly effective, other propellants well known to those skilled in the art may be used. The solution of estradiol and water-insoluble vinylpyrrolidone copolymer in ethanol may be pressurized in an aerosol can with a propellant. In order to control the amount of polymer and estradiol applied to the skin, it is advantageous to use a metering valve which delivers precise quantities of solution. When applied in this manner, the propellant and solvent quickly evaporate leaving a dry film of controlled estradiol content covering the desired area of skin.

A gel or thickened solution of estradiol and water-insoluble vinylpyrrolidone copolymer may be applied with greater control to a restricted area of skin than a low viscosity solution. The solution may be thickened by the addition of a small amount of a soluble high molecular weight inert polymer or a thickener of the type well known to those skilled in the art. High surface area inorganic materials such as finely divided fumed silica are particularly effective thickeners. The addition of a small amount of such a material results in a marked increase in the viscosity of the solution. The resultant gel or thickened solution exhibits thixotropy and flows readily during application but does not spread after application to the skin. The large surface area of the thickener increases the rate of evaporation of the solvent and contributes to rapid drying and film formation. The estradiol is slowly released and absorbed into the skin of the patient. At the end of the desired treatment period, or sooner if undesirable reaction to the estradiol is noted, the film may be removed by rubbing with soap and water or alcohol.

The gel or thickened solution may be applied to the skin in a pre-measured amount from a tube or a roll-on dispenser.

A solution or dispersion of uncrosslinked, water-insoluble vinylpyrrolidone copolymer and estradiol, in the absence or presence of an exipient, may be applied to a porous or open-structured substrate such as gauze, bandage tissue or paper, and upon evaporation of the solvent, provides an impregnated structure containing estradiol, which is released over an extended period of time when applied topically to the skin of a patient.

The solution or dispersion of water-insoluble vinylpyrrolidone copolymer and estradiol may be mixed, with stirring, with one or more ointment bases, such as petrolatum, vasoline, lanolin, stearin, spermaceti wax or other waxy or fatty material. The ointment may be applied directly to the skin of a patient or may be coated on a carrier such as a bandage or polymeric tape for topical application to the skin of a patient. The estradiol is slowly released and absorbed into the skin of the patient over an extended period of time.

Although the vinylpyrrolidone copolymer is water-insoluble, the hydrophilicity of the vinylpyrrolidone units contained therein results in moisture absorption, e.g. from perspiration on the skin of the patient, and extraction of the estradiol from the composition followed by absorption of the drug into the skin. The rate of extraction may be varied over a wide range and is dependent upon the concentration of vinylpyrrolidone in the copolymer.

The concentration of water-insoluble vinylpyrrolidone copolymer and estradiol in the compositions of the present invention, may be varied over a wide range, depending upon the desired release rate. The estradiol concentration may range from about 0.01% to about 1% of the total weight of the composition, while the concentration of the water-insoluble vinylpyrrolidone copolymer may range from about 5 to about 5000% of the weight of the estradiol.

The following examples are non-limiting illustrative embodiments of the compositions and methods of the present invention. Variations thereof will be obvious to those skilled in the art.

EXAMPLE I

The emulsion copolymerization of 66.7 parts of N-vinylpyrrolidone (VP) and 28.6 parts of lauryl methacrylate (LM) was carried out in 200 parts of water containing 5 parts of sodium stearate and 1.25 parts of 30% hydrogen peroxide as catalyst. The mixture was heated with stirring and the polymerization was carried out at 75° C. for about 10 hours. The conversion was 92%. The emulsion was spray dried at about 210° C. to yield a fine, off-white powder. The nitrogen content of the copolymer was 8.6%, indicating a VP content of 68%.

A gel base was prepared by dissolving 20 parts of the VP/LM copolymer in 64 parts of anhydrous ethanol with stirring at room temperature. To the above solution were added 6 parts of glycerin, 3 parts of high molecular weight polyvinylpyrrolidone and 6 parts of fumed silica. Estradiol-containing gels were prepared by mixing 0.1 or 0.25 parts of 17β-estradiol into 100 parts of the gel base. The resultant smooth gels were applied to the skin of patients from a tube by means of a graduated piece of cardboard. The gels dried completely after 3 minutes producing soft, pliable estradiol-containing films.

EXAMPLE II

An emulsion polymerization was carried out using the following ingredients, in parts by weight:

| Water | 22,100 |
|---|---|
| Stearic acid | 440 |
| Ammonium hydroxide (25%) | 192 |
| Isopropanol | 112 |
| N-Vinylpyrrolidone | 8,064 |
| Lauryl methacrylate | 3,456 |
| Sodium metabisulfite (6% aq. solution) | 425 |
| Hydrogen peroxide (30%) | 156 |

All of the ingredients except the sodium metabisulfite solution were charged into a stainless steel reactor equipped with heating jacket, condenser and mechanical stirrer. The bisulfite solution was added slowly over 5 hours, while maintaining the temperature at 75° C. with stirring. The reaction was then continued with stirring for an additional 4 hours at 75° C. and then the emulsion was permitted to cool to room temperature. The solids content was 32.5%, representing 94% conversion. The emulsion was diluted to 20% solids and spray dried at 210° C. to yield a fine, off-white powder which had a nitrogen content of 8.7%, equivalent to a VP content of 69%.

A gel was prepared by vigorously mixing the following ingredients, in parts by weight:

| VP/LM copolymer | 11.0 |
|---|---|
| Cetyl alcohol | 4.0 |
| Propylene glycol | 5.5 |
| Isopropyl myristate | 2.8 |
| Magnesium stearate | 1.0 |
| Sodium stearate | 3.8 |
| Fumed silica | 7.0 |
| Ethanol | 68.0 |

The resultant gel had a viscosity of 30,000-40,000 cps.

Estradiol-containing gels were prepared by mixing 100 parts of the base gel with 0.05 to 1.0 part of estradiol. The resultant formulation was packed into aluminum tubes and applied to the skin of various menopausal patients having very low endogenous estradiol. The application of 1.5 grams of the gel was made once a day.

The estradiol content (E2) in the plasma was determined periodically.

| Patient | A | B | C | D |
|---|---|---|---|---|
| Estradiol in gel, % | 0.05 | 0.1 | 0.5 | 1.0 |
| Estradiol in plasma, pg/ml | | | | |
| Initial | 22 | <10 | 37 | 25 |
| After 3 days | 46 | 64 | 67 | — |
| After 5 days | — | — | — | 83 |
| After 21 days | — | — | 70 | — |

EXAMPLE III

An emulsion polymerization was carried out with the following charge, in parts by weight:

| Water | 23,042 |
|---|---|
| Emulsifier* | 460 |
| Ammonium hydroxide (25%) | 75 |
| N-Vinylpyrrolidone | 9,288 |
| Lauryl methacrylate | 3,981 |
| Hydrogen peroxide (30%) | 339 |
| Sodium metabisulfite | 53 |
| Water | 979 |

*Ammonium salt of sulfated ester of alkylphenoxypoly(ethyleneoxy)ethanol (Alipal CO436

The first six ingredients were charged into the reactor and the sodium metabisulfite solution was added over 10 hours while the temperature was maintained at 75° C., as described in Example II. After 11 hours the conversion was 96.2%. The emulsion was spray dried and the fine powder had a VP content of 66.1%. After the powder was placed in an oven for 24 hours at 90° C., the free monomer content was found to be 0.03% VP and 0.23% LM.

A gel was prepared from the following ingredients, in parts by weight:

| | |
|---|---|
| VP/LM copolymer | 7.0 |
| Hydroxypropylcellulose | 1.0 |
| Cetyl alcohol | 1.9 |
| Propylene glycol | 1.0 |
| Isopropyl myristate | 1.4 |
| Magnesium stearate | 0.5 |
| Sodium stearate | 1.5 |
| Fumed silica | 2.0 |
| Ethanol | 83.7 |

Gels were prepared by mixing 100 parts of the base gel with either 0.5 or 1.0 part of 17β-estradiol. The resultant gel was packed in aluminum tubes for clinical studies.

The gel containing 1.0% estradiol was applied once a day using a graduated cardboard to a group of menopausal patients. The dosage varied from 0.5 to 1.5 grams of gel per application. The initial and final levels of estradiol in the plasma were determined.

| Patient | Daily Dose (grams) | Time (days) | Estradiol, pg/ml | |
|---|---|---|---|---|
| | | | Initial | Final |
| 1 | 1.5 | 9 | 25 | 83 |
| 2 | 1.5 | 3 | 23 | 111 |
| 3 | 0.5 | 9 | 20 | 70 |
| 4 | 1.5 | 19 | 20 | 11 |
| 5 | 1.5 | 16 | 20 | 200 |
| 6 | 0.5-1.5 | 5 | 25 | 47 |
| 7 | 0.5-1.5 | 5 | 20 | 86 |
| 8 | 0.5-1.5 | 5 | 22 | 98 |

EXAMPLE IV

The solution copolymerization of 64 parts of N-vinylpyrrolidone (VP) and 36 parts of 2-ethylhexyl acrylate (EHA) was carried out in 100 ml of isopropanol using one part of lauroyl peroxide as catalyst. The catalyst was added as part of the initial charge and the polymerization was carried out under reflux, with stirring over a period of 12 hours. The conversion was 95%. The copolymer solution was cast on a sheet of polytetrafluoroethylene, air dried for several hours and then dried in an air oven at 60° C. The nitrogen content of the product was 8.4% indicating a VP content of 66%.

A gel was prepared from the VP/EHA copolymer using the recipe shown in Example III. The base gel was mixed with 1.0 part of 17β-estradiol per 100 parts of base gel and charged into a roll-on dispenser.

Application of the estradiol-containing gel to the skin of menopausal patients at a dosage of 1.5 grams per day maintained the estradiol content of the blood plasma at 50 to 150 pg/ml.

EXAMPLE V

The gel containing 1% 17β-estradiol, prepared in accordance with the recipe in Example III, was packed into roll-on plastic containers and tested on patients immediately after hysterectomy plus bilateral salpingo-oophorectomy.

An 0.8 gram dosage of the gel was applied to the skin of the patients on a daily basis and the treatment was continued for a period of 1 to 2 years.

| Patient | | Treatment Time, years | Estradiol in plasma, pg/ml | |
|---|---|---|---|---|
| | | | Range | Mean |
| Menopause | (A) | 2 | 50-100 | 80 |
| Surgical menopause | (B) | 2 | 100-250 | 150 |
| Surgical menopause | (C) | 1 | 60-150 | 120 |
| Menopause | (D) | 1 | 40-150 | 110 |

EXAMPLE VI

A gel base was prepared from VP/LM copolymer, in accordance with Example I. Separately, a gelatinous mixture was prepared from 65 grams of polyethylene glycol with a molecular weight of 300 with 35 grams of polyethylene glycol with a molecular weight of 4000.

VP/LM copolymer gel bases were mixed with estradiol benzoate (0.5%) (A) and ethinylestradiol (0.01%) (B). Similar compositions were prepared by mixing the polyethylene glycol gel with 0.5% estradiol benzoate (C) and 0.01% ethinylestradiol (D).

The rate of diffusion of the estradiol derivatives through a skin membrane was measured in a standard diffusion cell, using isotonic saline as the reception solution. Preparations A and B containing the VP/LM copolymer showed rates of diffusion about one order of magnitude lower than the corresponding copolymer-free preparations C and D.

What is claimed is:

1. A composition for the sustained transdermal administration of an estrogen selected from the group consisting of 17β-estradiol, ethinylestradiol and 17β-estradiol esters, comprising an ointment base, gel or film containing a mixture of the estrogen and an uncrosslinked, water-insoluble vinylpyrrolidone copolymer containing at least 10% by weight vinylpyrrolidone and a comonomer which is copolymerizable therewith by free radical polymerization, wherein the estrogen concentration is within the range of about 0.01% to about 1% of the total weight of the composition.

2. A composition for the sustained transdermal administration of an estrogen selected from the group consisting of 17β-estradiol, ethinylestradiol and 17β-estradiol esters, comprising an ointment base, gel or film containing a mixture of the estrogen and an uncrosslinked, water-insoluble vinylpyrrolidone copolymer which contains at least 10% by weight vinylpyrrolidone and units derived from an ester of an unsaturated acid selected from the group consisting of acrylic acid, methacrylic acid, crotonic acid, maleic acid and the corresponding anhydrides, wherein the estrogen concentration is within the range of about 0.01% to about 1% of the total weight of the composition.

3. The composition of claim 2, wherein the ester is selected from the group consisting of the acrylic and methacrylic esters of $C_1$ to $C_{40}$ linear and branched alkanols.

4. The composition of claim 2, wherein the ester is lauryl methacrylate.

5. The composition of claim 2, wherein the ester is 2-ethylhexyl acrylate.

6. A composition for the sustained transdermal administration of an estrogen selected from the group consisting of 17β-estradiol, ethinylestradiol and estradiol esters, comprising an ointment base, gel or film containing a mixture of the estrogen and an uncrosslinked, water-insoluble vinylpyrrolidone copolymer which contains at least 10% by weight vinylpyrrolidone and units derived from an ester of a saturated acid selected from the group consisting of the vinyl and allyl esters of $C_1$ to $C_{40}$ carboxylic acids, wherein the estrogen concentration is within the range of about 0.01% to about 1% of the total weight of the composition.

7. The composition of claim 6, wherein the ester is vinyl acetate.

8. A composition for the sustained transdermal administration of an estrogen selected from the group consisting of 17β-estradiol, ethinylestradiol and 17β-estradiol esters, comprising an ointment base, gel or film containing a mixture of the estrogen and an uncrosslinked, water-insoluble vinylpyrrolidone copolymer with styrene, wherein the copolymer contains at least 10% by weight vinylpyrrolidone, and wherein the estrogen concentration is within the range of about 0.01% to about 1% of the total weight of the composition.

9. The composition of claim 6, wherein the water-insoluble vinylpyrrolidone copolymer contains units derived from an unsaturated acid selected from the group consisting of acrylic acid, methacrylic acid, crotonic acid, maleic acid and the corresponding anhydrides.

10. The composition of claim 1, wherein the estrogen and water-insoluble vinylpyrrolidone copolymer are combined with an ointment base.

11. The composition of claim 2, wherein the estrogen and water-insoluble vinylpyrrolidone copolymer are combined with an ointment base.

12. The composition of claim 6, wherein the estrogen and water-insoluble vinylpyrrolidone copolymer are combined with an ointment base.

13. A bandage, gauze or tape impregnated or coated with the composition of claim 10.

14. A bandage, gauze or tape impregnated or coated with the composition of claim 11.

15. A bandage, gauze or tape impregnated or coated with the composition of claim 12.

16. The composition of claim 1, wherein the estrogen and water-insoluble vinylpyrrolidone copolymer are combined with a solvent and a thickener to generate a gelled composition.

17. The composition of claim 2, wherein the estrogen and water-insoluble vinylpyrrolidone copolymer are combined with a solvent and a thickener to generate a gelled composition.

18. The composition of claim 6, wherein the estrogen and water-insoluble vinylpyrrolidone copolymer are combined with a solvent and a thickener to generate a gelled composition.

19. A method for providing for the sustained transdermal administration of an estrogen selected from the group consisting of 17β-estradiol, ethinylestradiol and 17β-estradiol esters, which comprises applying to the skin of a patient, a solution containing the estrogen and an uncrosslinked water-insoluble vinylpyrrolidone copolymer which contains at least 10% by weight of vinylpyrrolidone and a comonomer which is copolymerizable therewith by free radical polymerization.

20. The method of claim 19, wherein the solution is applied to the skin of a patient in the form of an aerosol.

* * * * *